(12) United States Patent
Schuch et al.

(10) Patent No.: US 6,562,307 B1
(45) Date of Patent: May 13, 2003

(54) PROCESS AND APPARATUS FOR THE PARALLEL ANALYSIS OF COLLOIDAL PARTICLES USING FIELD-FLOW FRACTIONATION

(75) Inventors: Horst Schuch, Heidelberg (DE); Wolfgang Schrof, Neuleiningen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/610,944

(22) Filed: Jul. 6, 2000

(30) Foreign Application Priority Data

Jul. 8, 1999 (DE) .......................................... 199 31 901

(51) Int. Cl.[7] .............................................. B01D 11/04
(52) U.S. Cl. ...................... 422/256; 422/68.1; 422/81; 422/82; 422/255; 436/161
(58) Field of Search ........................ 436/161; 422/68.1, 422/81, 82, 255

(56) References Cited

U.S. PATENT DOCUMENTS

| | | | | |
|---|---|---|---|---|
| 4,204,929 A | * | 5/1980 | Bier ............................ 204/518 |
| 4,234,404 A | * | 11/1980 | Satoh .......................... 204/644 |
| 4,414,106 A | * | 11/1983 | Romanauskas ............. 209/155 |
| 4,440,638 A | * | 4/1984 | Judy et al. ................... 204/672 |
| 4,539,040 A | * | 9/1985 | Mawardi ................. 423/658.5 |
| 4,631,687 A | * | 12/1986 | Kowalski et al. .............. 702/28 |
| 4,657,676 A | * | 4/1987 | Keary et al. ............. 210/198.2 |
| 4,708,782 A | * | 11/1987 | Andresen et al. ........... 210/192 |
| 4,737,268 A | * | 4/1988 | Giddings .................... 209/12.2 |
| 4,834,862 A | * | 5/1989 | Breiner et al. ............... 204/548 |
| 4,874,507 A | * | 10/1989 | Whitlock ...................... 209/11 |
| 5,240,618 A | * | 8/1993 | Caldwell et al. ............. 210/748 |
| 5,716,852 A | * | 2/1998 | Yager et al. ................. 436/172 |
| 5,906,724 A | * | 5/1999 | Sammons et al. ........... 204/627 |
| 5,932,100 A | * | 8/1999 | Yager et al. ................. 210/634 |
| 6,124,138 A | * | 9/2000 | Woudenberg ............... 436/518 |
| 6,136,171 A | * | 10/2000 | Frazier et al. .............. 204/450 |
| 2001/0000103 A1 | * | 4/2001 | Rhodes ........................ 204/454 |

OTHER PUBLICATIONS

J.C. Giddings "Measuring Colloidal and Macromolecular Properties by FFF" Analytical Chemistry (1995) p. 592A.
Michael Martin "Advances in Chromatography" vol. 39 (1998) pp. 1–138.

* cited by examiner

*Primary Examiner*—Jill Warden
*Assistant Examiner*—Yelena Gakh
(74) *Attorney, Agent, or Firm*—Keil & Weinkauf

(57) ABSTRACT

The present invention relates to an apparatus for the simultaneous analysis of at least two samples by the field-flow fractionation method, where the apparatus has at least the following elements:

a) a source of a defined liquid stream, preferably a pump,
b) at least two separation channels, each with at least one inlet and each with at least one outlet for passing the at least two samples through in each case one of the at least two separation channels,
c) at least one controllable unit which is connected to the at least two separation channels via their at least one outlet each, and which can pass on the at least two samples, which can be passed through in each case one of the at least two separation channels, separately from one another to at least one unit downstream of the controllable unit.

4 Claims, 1 Drawing Sheet

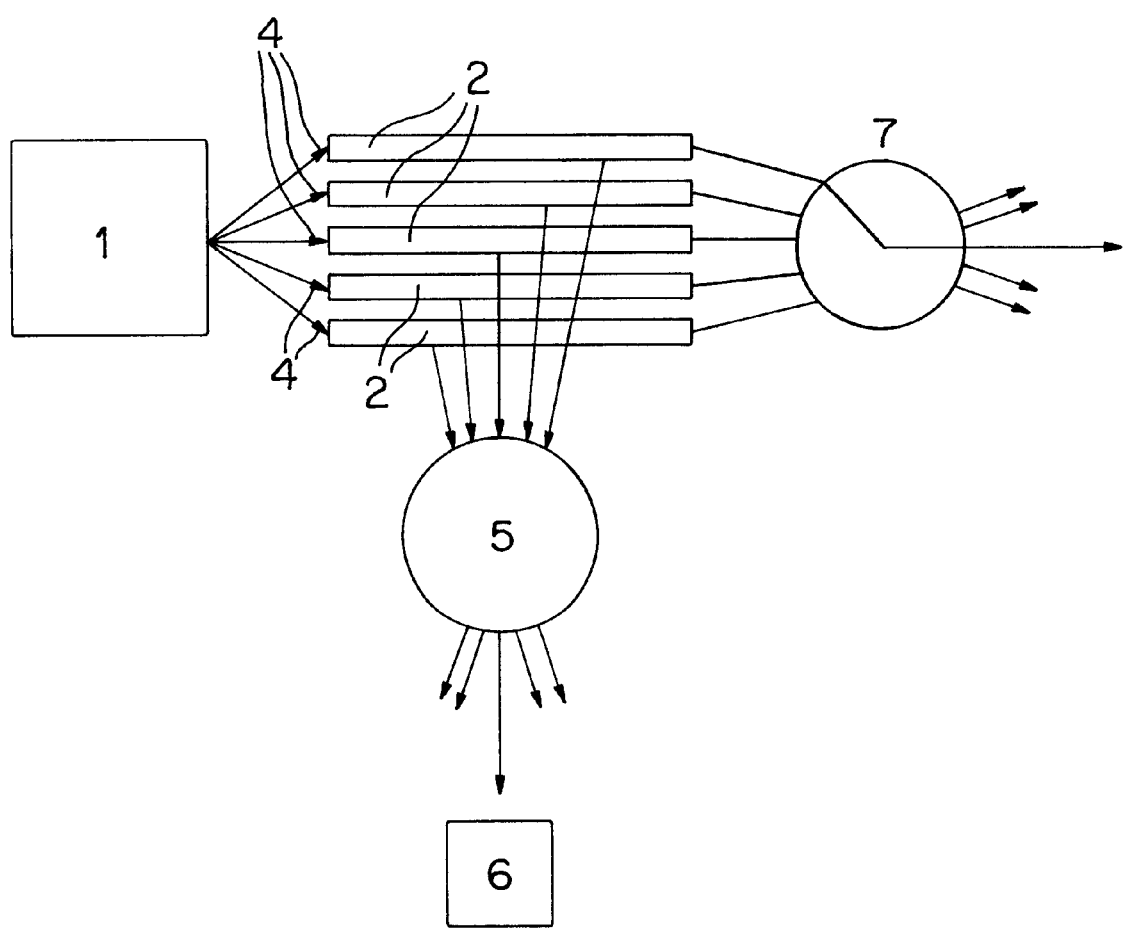

PROCESS AND APPARATUS FOR THE PARALLEL ANALYSIS OF COLLOIDAL PARTICLES USING FIELD-FLOW FRACTIONATION

BACKGROUND OF THE INVENTION

The present invention relates to an apparatus and a process for the simultaneous analysis of a plurality of samples containing colloidal particles by means of the field-flow fractionation method.

The field-flow fractionation method is a separation and measurement method which has already been known, for some time and goes back to J. C. Giddings and which is used in particular in the analysis of colloidal particles, for a number of polymers, for biological macromolecules and for a wide variety of polymer complexes [J. C. Giddings, *Anal. Chem.* 67 (1995), 592A]. The field-flow fractionation method is often referred to as "one-phase chromatography" since the separation of the various particles to be separated takes place within a single phase. This phase is preferably a liquid phase.

The field-flow fractionation method profits from an essentially very simple analysis arrangement. The field-flow fractionation is preferably carried out within a narrow, shallow channel through which a constant stream of liquid is passed and maintained. A laminar flow profile is created here [Michel Martin, *Advances in Chromatography* (N.Y.), 1998, Vol. 39, 1–138]. As the second basic prerequisite for the performance of the field-flow fractionation method, a transverse force field or a transverse flow stream is superimposed on this flow profile. Through a combination of the laminar axial flow profile with the transversely superimposed force field or the transversely superimposed flow stream, samples containing different types of particle present in the carrier liquid can, utilizing the different effect of the resultant force field or flow stream on the different constituents of the samples, be divided spatially into precisely these different constituents. Fractionation takes place as a function of the hydrodynamic diameter (flow field-flow fractionation) or in other field-flow fractionation methods as a function of the chemical composition or density or charge, this usually being combined with the hydrodynamic diameter.

In general, a distinction can be made between four different techniques in the field-flow fractionation method, depending on the type of transversely applied force field. These are the following:

flow field-flow fractionation, sedimentation field-flow fractionation, thermal field-flow fractionation and electrophoretic field-flow fractionation.

An example which may be mentioned is flow field-flow fractionation. In flow field-flow fractionation, a transverse flow stream of the carrier liquid takes on the role of the force field. With the aid of flow field-flow fractionation, the coefficient of friction of the particles to be analyzed, their hydrodynamic diameter and the diffusion coefficient can be determined directly from the following conditional equation chain:

$$F_{flow\ stream} = fU = 3\pi\eta d_h U = (kT/D)U$$

where f=coefficient of friction

U=transverse flow rate $\eta$=viscosity $d_h$=hydrodynamic diameter k=Boltzmann constant T=absolute temperature D=diffusion coefficient.

Some measurement inaccuracy in flow field-flow fractionation is caused by uneven wall surfaces or compressible membranes serving as accumulation wall. This is preferably countered by appropriate calibration by means of a known diffusion coefficient or particularly preferably by coupling flow field-flow fractionation with one or more on-line detector(s).

Besides the parameters obtainable directly, further parameters, for example the molecular weight or gyration radii of polymers, can also be determined by means of appropriate models, assumptions or other prior knowledge regarding the particles to be analyzed.

Hitherto, when applying the field-flow fractionation method to the analysis of a sample, use has always been made of only a single separation channel, into which the sample was injected, transported through the channel by the carrier liquid and divided into individual zones, as explained above, during passage through the channel, depending on the choice of the specific field-flow fractionation method, these zones then ultimately allowing information to be provided on the individual particles present in the sample to be analyzed. Besides the separation channel, this required an extensive set of further peripherals, for example, inter alia, a pump for the carrier liquid, a further pump for the injection of the sample to be analyzed into the separation channel, depending on the analysis aim at least one detector or a further measurement or analysis unit coupled to the separation channel. Suitable detectors are, for example, all detectors from gel permeation chromatography (GPC), for example refractive index detectors (RI detectors), infra-red detectors (IR detectors), UV-VIS detectors, fluorescence detectors, light scattering detectors, Raman detectors, MALDI detectors and evaporation light scattering detectors. Furthermore, a storage container for the carrier liquid is provided. In addition, high quality demands are made of the separation channel, for example the requirement for an extremely pressure-stable construction so that the liquid streams remain stable in the narrow channels.

If, for example, the flow field-flow fractionation method is considered for the determination of the size distribution of colloidal particles in a sample to be analyzed, the procedure adopted hitherto was to inject in each case one sample into a separation channel coupled to a corresponding set of peripherals. The separation channel corresponded to a shallow channel, typically with a length of from about 1 cm to 100 cm and a depth in the range from about 0.1 mm to 0.4 mm. At least one of the walls delimiting the channel was a semi-permeable membrane, which was permeable to the carrier liquid, but impermeable to the particles present in the sample. After injection of the sample into the separation channel, the sample was firstly focused on an area inside the separation channel. This is achieved, for example, by pumping the carrier liquid into the channel from both ends of the channel, i.e. both from the inlet and from the future outlet, immediately after injection of the sample, so that the sample is initially concentrated in an area within the channel. Due to the action of the transverse flow stream as employed in flow field-flow fractionation, the sample or the particles present therein is transported in the direction of the accumulation wall, which corresponds here to the semi-permeable wall, and is initially concentrated there. The diffusion motion of the particles then commences in the opposite direction to the transverse flow stream and to different degrees depending on the particle type and/or size. When an equilibrium has been reached between the transverse flow stream and the corresponding diffusion motion, the respective particles come to a "stop" at a certain point or in a certain, particle-dependent zone within the channel cross section; the particles have then reached their equilibrium position with respect to transverse motion. Depending on the position within the cross section, they are then transported through the channel at different speeds by the carrier liquid, which is pumped into the channel from the inlet side of the separation channel with a flow profile which is not uniform with respect to the channel cross section, i.e. the various particles have different residence times within the separation channel. The residence time as an actual parameter ultimately allows conclusions to be drawn on the respective forces acting on the particles within the channel, taking into account the known non-uniform flow profile of the carrier liquid, as explained above, and in turn, according to the abovementioned conditional equilibrium chain, allows information to be obtained on specific parameters, for example the hydrodynamic diameter. The duration of the measurement for particles of a single type is in the range from less than one minute to about 2 hours, depending on the sample type and on the structure of the separation channel.

A disadvantage here is that it has hitherto appeared impossible to measure quickly and accurately a plurality of samples to be compared with one another. For the analysis of a whole series of samples which were to be compared with one another, the field-flow fractionation method was consequently not suitable, since the procedure known hitherto was much too slow and consequently much too ineffective. In addition, it would have been necessary to create precisely the same analysis conditions for each new sample to be analyzed in order to be able to ensure any later meaningful comparison of the results of the individual samples. In addition, the requisite calibration procedures would have taken a considerable amount of time.

However, it is desirable in many analyses to test and compare a whole series of samples with one another as quickly as possible and nevertheless reliably. A "screening" of this type is essentially used in the optimization of certain selected parameters of one or more types of particle. One desired aim is, for example, to find an effective screening method for the optimization and monitoring of the size distribution, in particular of colloidal particles and/or of the particle type. The following particles may be mentioned here by way of example: solid particles, vesicles, gel particles, natural and synthetic polymers, protective colloids, associates, micelles, block and random copolymers, hybrid particles having a diameter of $\leq 10$ $\mu$m, for example micronizates, pigments, proteins, starches and sugars.

It is an object of the present invention to provide an apparatus and a process for the screening or parallel analysis of a plurality of particles to be investigated, in particular samples containing colloidal particles, with it being possible to obtain reliable and accurate information regarding the particles quickly.

We have found that this object is achieved by an apparatus as claimed in claim 1 and a process as claimed in claim 7. Preferred embodiments of the present invention are given in the sub-claims. The invention furthermore relates to the use of the apparatus according to the invention and of the process according to the invention for the optimization and/or monitoring of the size distribution of particles, in particular of colloidal particles and/or of the particle type.

DETAILED DESCRIPTION OF THE INVENTION

The invention provides an apparatus for the simultaneous analysis of at least two samples by the field-flow fractionation method, where the apparatus has at least the following elements:

a) a source of a defined liquid stream, preferably a pump,
b) at least two separation channels, each with at least one inlet and each with at least one outlet for passing the at least two samples through in each case one of the at least two separation channels,
c) at least one controllable unit which is coupled to the at least two separation channels via their at least one outlet each in such a way that with their aid the at least two samples which can be passed through in each case one of the at least two separation channels can be passed on, separately from one another, to at least one unit downstream of the controllable unit.

The apparatus preferably comprises a whole series of identical separation channels. The number of separation channels is in the range from 2 to more than 1000.

The controllable unit is preferably one or more multi-port valves which are coupled to each separation channel. With the aid of the multi-port valve, it is possible, in accordance with a definable or controllable or adjustable time cycle, to connect in each case one separation channel to a unit downstream of the multi-port valve or to pass a sample which has been passed through this separation channel on to a unit downstream of the multi-port valve and thus to subject it to a further analysis. Owing to the use according to the invention of a multi-port valve, different samples passed simultaneously through different separation channels are prevented from coming into contact with one another and/or mixing with one another. It is not absolutely necessary for a dividing wall to be present between the individual separation channels since flow streams are generally laminar. Through the construction of the apparatus according to the invention, it is possible to provide only one set of peripherals in addition to the multiplicity of separation channels. The apparatus according to the invention preferably comprises only one pump for passing the carrier liquid through the various separation channels. In accordance with the invention, the pump here is preferably connected in each case to one of the multiplicity of separation channels via a regulation valve. The regulation valve is preferably time-controllable. Besides a considerable cost saving, this apparatus construction ensures that the requisite introduction and transport of the carrier liquid into and through the individual separation channels can always be carried out with the same pressure, which is a basic prerequisite for later comparison of the results obtained for the individual samples with one another. The advantage of the coupling of a plurality of separation channels to one another consists in an essentially higher sample throughput, at the same time lower costs and the comparability of samples which are unstable or changeable over time that this facilitates. This is necessary for a CMR (CMR=combinatorial materials research) capability, namely the balance between the parallel production of samples and the subsequent characterization by field-flow fractionation.

In a preferred embodiment of the apparatus according to the invention, the controllable unit with the aid of which the samples passed through the various separation channels can be passed on is followed by one or more detectors.

In a further preferred embodiment of the invention, other analysis units are provided in addition to detectors.

In a preferred embodiment, the analysis unit in the apparatus according to the invention, to which the samples divided after passage through the respective separation channels are fed, is a microscope, preferably a light microscope.

In another preferred embodiment, the apparatus according to the invention has devices for carrying out photon correlation measurements.

Furthermore, a further preferred embodiment of the apparatus according to the invention comprises devices for carrying out analytical methods, based on light scattering.

In another preferred embodiment of the apparatus according to the invention, the field-flow fractionation method is flow field-flow fractionation. To this end, a transverse flow stream is provided in addition to the axial flow of the carrier liquid. In a preferred embodiment of the invention, the transverse flow stream, after passing through the separation channels, is discharged via a multi-port valve to a flow meter, preferably to a flow meter with a small pressure drop. The outlet lines are preferably provided with a flow resistance in such a way that the pressure drop corresponds to that of the downstream flow meter. In a further preferred embodiment of the apparatus according to the invention, the discharge of the transverse flow stream does not take place via a multi-port valve, but instead by means of a piston pump operating a plurality of pistons in parallel.

In a further preferred embodiment of the apparatus according to the invention, the field-flow fractionation method is sedimentation field-flow fractionation or thermal field-flow fractionation or electrophoretic field-flow fractionation.

In a further preferred embodiment of the apparatus according to the invention, the at least two separation channels are arranged in a sandwich structure. This arrangement of the channels simplifies the requisite pressure-stable construction of the individual channels. In addition, this arrangement simplifies temperature control of the individual separation channels. The separations of the corresponding samples to be carried out within the individual separation channels are preferably carried out at temperatures above 25° C., for example in the range from about 60° C. to above 200° C.

In a further preferred embodiment of the apparatus according to the invention, the at least two separation channels are connected in parallel. In this case, at least two separation channels are preferably covered by a large-area membrane. This particularly preferably has at least two inlets for the at least two samples to be passed through in each case one of the at least two separation channels. This likewise allows considerable cost savings to be made. The at least two separation channels are in this case separated from one another merely by the flow stream with the carrier liquid, i.e. the separation channels are not separated from one another by a physical separation device, for example a dividing wall. There are consequently no peripheral zones in the flow stream, which considerably improves the separation efficiency and ensures that the flow conditions are virtually identical in the various separation channels. The prerequisite for preventing the various samples from coming into contact with one another is merely that the particles present in the sample to be analyzed are not too small, so that they only exhibit very slight diffusion. Preference is given to the analysis of particles having a size of $\geq 10$ nm.

The membrane used in accordance with the invention can be either an elastic membrane or a solid membrane, for example a ceramic membrane.

In a further preferred embodiment of the apparatus according to the invention, the separation channels have a reduced length, preferably a length reduced by a factor of 5. This enables the analysis time for a separation channel to be significantly reduced at the cost of a slight drop in separation efficiency which is acceptable for a screening apparatus.

The invention furthermore relates to a process for the simultaneous analysis of at least two samples containing colloidal particles, the process having at least the following steps:

a) introduction of the at least two samples into in each case at least one separation channel, b) simultaneous exertion of a force acting perpendicular to the axial direction of the respective separation channel onto the at least two samples, c) controllable, separate passing-on of the at least two samples from the respective at least one separation channel to at least one further unit.

The process is preferably one of the abovementioned different field-flow fractionation methods, i.e. either flow field-flow fractionation or sedimentation field-flow fractionation or thermal field-flow fractionation or electrophoretic field-flow fractionation.

The present invention furthermore relates to the use of the process according to the invention and/or of the apparatus according to the invention for the fractionation of particles, in particular of colloidal particles, in accordance with their diameter or in accordance with other properties, in particular in accordance with the chemical composition or the density or the charge, or in accordance with combinations thereof.

In accordance with the invention, all possible colloidal particles can be analyzed or fractionated. The term "colloidal particles" here covers particles having a diameter in the range from 1 to 5000 nm, preferably from 1 to 1000 nm, which are dispersed in a liquid or gaseous phase. Of these, particular mention may be made of the following:

synthetic or natural polymers which are branched, partially crosslinked or have a tertiary structure, for example proteins, compact or hollowed dispersion particles, if desired comprising a protective colloid and/or an active ingredient;

spherical and aspherical associates of polymers, oligomers (micelles) and other colloidal particles;

spherical and aspherical particles, if desired comprising a protective colloid, of either organic, biological or inorganic origin.

Further advantages and properties of the invention are indicated below with reference to a working example of the present invention in conjunction with the following figure, in which:

DESCRIPTION OF THE DRAWING

FIG. 1 shows a diagrammatic representation of the structure of an apparatus according to the invention.

FIG. 1 shows an apparatus according to the invention which can be used for the simultaneous analysis of a plurality of samples by flow field-flow fractionation. With the aid of a pump 1, a suitable carrier liquid is pumped into each of the separation channels 2. The inlet 4 for the carrier liquid for each separation channel 2 is preferably fitted with a flow control valve. It can thus be ensured that the carrier liquid is passed into and through each separation channel 2 at the same pressure. Identical flow conditions with respect to the carrier liquid are thus created in each separation channel 2, with the prerequisite that all separation channels have the same structure, which enables a direct comparison of the analysis results. The sample is preferably likewise introduced through the lines 3 by means of switching valves, as usually used in GPC, or through other inlet devices conventional in flow field-flow fractionation, at the inlet 4 to each separation channel. Sample introduction at the outlet of the separation channels is also possible. At the same time as the axial flow, the apparatus according to the invention has a transverse flow stream in accordance with the prerequisites for carrying out the flow field-flow fractionation method. The transverse flow steam is preferably fed to a flow meter 6 via correspondingly provided outline lines via a multi-port valve 5. In a preferred embodiment, the flow meter has a small pressure drop. Furthermore, in a preferred embodiment of the apparatus according to the invention, all outlet lines for the transverse flow stream have a flow resistance, so that the pressure drop corresponds to that of the flow meter. The samples passed through the corresponding separation channels 2 with the axial flow of the carrier liquid can, after passing through in each case one separation channel, be connected via a further multi-port valve 7 to one or more further analysis or measurement units. These are preferably one or more detectors. The multi-port valve 7 preferably connects the individual separation channels 2 to the detector (s) in accordance with a fixed, adjustable time cycle.

We claim:

1. An apparatus for the simultaneous analysis of at least two samples by the flow field-flow fractionation method, where the apparatus has at least the following elements:
   a) as a source of a defined liquid stream, a pump,
   b) at least two separation channels, each with at least one inlet and each with at least one outlet for passing each sample through in each case one of the at least two separation channels, wherein the pump is connected in each case to one of the at least two separation channels via a regulation valve,
   c) at least one controllable unit which is connected to the at least two separation channels via their at least one outlet each, and which can pass on the at least two samples, which can be passed through in each case one of the at least two separation channels, separately from one another to at least one unit downstream of the controllable unit,
   d) and in which the at least two separation channels are separated from one another merely by the flow stream with the carrier liquid, with the prerequisite that the particles present in the samples to be analyzed have a size of $\geq 10$ nm, wherein a membrane simultaneously covers the at least two separation channels.

2. An apparatus as claimed in claim 1, wherein the controllable unit has one or more multi-port valves.

3. An apparatus as claimed in claim 1, wherein the at least one unit downstream of the controllable unit is a detector.

4. An apparatus as claimed in claim 1, wherein the membrane is an elastic membrane or a solid membrane.

* * * * *